United States Patent [19]

Sandbank

[11] Patent Number: 4,928,680
[45] Date of Patent: May 29, 1990

[54] ADHESIVE COATED DRESSING AND APPLICATORS THEREFOR

[75] Inventor: Barry M. Sandbank, Herts, United Kingdom

[73] Assignee: Smith & Nephew plc, United Kingdom

[21] Appl. No.: 242,727

[22] Filed: Sep. 9, 1988

[30] Foreign Application Priority Data

Sep. 15, 1987 [GB] United Kingdom ............... 8721659

[51] Int. Cl.⁵ ............................................. A61F 13/00
[52] U.S. Cl. ..................................... 128/155; 128/156
[58] Field of Search .............................. 128/155, 156

[56] References Cited

U.S. PATENT DOCUMENTS

| | | | |
|---|---|---|---|
| 247,064 | 1/1978 | Spiegelberg | 128/156 X |
| 2,469,064 | 5/1949 | Campbell | 128/156 |
| 4,176,664 | 12/1979 | Kalish | 128/156 |
| 4,413,621 | 11/1983 | McCracken et al. | 128/156 |
| 4,598,004 | 7/1986 | Heinecke | 128/156 X |
| 4,614,183 | 9/1986 | McCracken et al. | 128/155 X |
| 4,664,106 | 5/1987 | Snedeker | 128/156 |
| 4,666,441 | 5/1987 | Andriola et al. | |
| 4,706,662 | 11/1987 | Thompson | 128/155 |
| 4,744,355 | 5/1988 | Faasse, Jr. | |

FOREIGN PATENT DOCUMENTS 2566266 6/1984 France .
2157955 4/1985 United Kingdom .

Primary Examiner—Richard J. Apley
Assistant Examiner—N. Paul
Attorney, Agent, or Firm—Jacobs & Jacobs

[57] ABSTRACT

An adhesive coated thin film dressing (1) in combination with an applicator (4) to facilitate its application is described. The applicator (4) comprises a pair of superimposed laminar members (5,6) hinged at one end. The lower member (6) is adapted to be grasped at the end (13) remote from the hinge (7). The upper member (5) supports the thin film dressing and is in releasable contact with a major portion of the adhesive surface (3) of the thin film (2). A protector (11) is in releaseable contact with the remaining portion of the adhesive surface (3) and extends beyond the hinged end of the upper member (5). In one preferred form the dressing has a medicated pad or a medicated area located on the adhesive side of the coated film.

12 Claims, 2 Drawing Sheets

ADHESIVE COATED DRESSING AND APPLICATORS THEREFOR

The invention relates to thin flexible film adhesive coated dressings and applicators therefor.

Conventional thin flexible film adhesive coated dressings such as wound dressings, incise drapes and catheter dressings usually have a protector over the adhesive coating. The dressings can be applied to a patient by removing the protector from the adhesive coating and adhering the dressing to the skin at the chosen site. These dressings are normally sufficiently conformable to skin to render them comfortable to wear In the past, application to the skin of such conformable dressings and in particular highly conformable dressings which comprise a thin elastomeric film has been found difficult to achieve without touching the adhesive or causing puckering or creasing of the adhesive coated film. Several dressings and applicator arrangements have been proposed to overcome these problems. It is known to provide a pair of non-adhesive handles at opposed edges of the adhesive dressing to facilitate its removal from the protector and application to the skin. The adhesive coated film of such a dressing, however, is not supported during its application and the dressing usually requires two hands to apply it to the patient. United Kingdom Patent Application No. GB 2128479A discloses a transparent film adhesive coated dressing which has a protector comprising two release sheets each provided with a tab so that the release sheets can be peeled from the middle to the side edges of the dressing to expose the adhesive coating at the middle portion of the dressing to enable that portion to be applied before the side portions are adhered. United Kingdom Application No. GB 2157955A discloses a flexible polymer film adhesive coated wound dressing which has removable main protector over its adhesive surface and an adhesive handle attached to an edge margin of the dressing which is covered by a separate protector. This patent further discloses that the adhesive handle can be adhered to the patient to serve as an anchor so that both hands are available to manoeuvre the dressing into position and remove the main protector prior to adhering it to the skin.

An alternative adhesive dressing and applicator arrangement has now been found which allows the dressing to be positioned accurately and applied to a patient without undue handling of the dressing.

Accordingly the present invention provides an adhesive coated thin film dressing in combination with an applicator therefor wherein the applicator comprises a pair of superposed laminar members hinged at one end, the lower member being adapted to be grasped at the end remote from the hinge and the upper member being adapted to support the dressing and being in releasable contact with a major portion of the adhesive surface thereof; and wherein a protector, in releasable contact with the remaining portion of the adhesive surface, extends beyond the hinged end of the upper member.

The dressing of the invention can be applied to a patient by removing the protector to expose an adhesive end portion of the dressing, adhering this portion to the skin to anchor the dressing and then grasping and pulling the lower member of the applicator to expose the major portion of the adhesive surface and adhere the remainder of the dressing to the skin.

The lower member is preferably sufficiently rigid to support the upper member bearing the dressing to enable the dressing, after removal of the protector to be positioned accurately on the treatment area and to be applied to the skin in controlled manner without handling the dressing. Furthermore, such an application may be achieved using one hand.

The portion of the adhesive surface of the dressing covered by the protector can conveniently be a marginal end portion of the dressing. Removal of the protector from such a portion can expose a marginal end adhesive portion of the dressing which can be adhered to the skin to provide an anchor to apply the remainder of the adhesive dressing under light tension to the skin. Typically the protector may extend beyond the adhesive surface of the marginal end portion of the dressing to provide a tab to facilitate removal thereof from the adhesive surface. The extended protector or tab may project beyond the end of the dressing or overlap the lower member at the hinged end of the applicator.

Advantageously the end portion of dressing covered by the protector can be stiffened to inhibit the end portion "drooping" when the protector layer is removed and thereby facilitate adhering the portion to the skin. The stiffened end portion of the dressing can be provided by a variety of methods including use of a stiffer film portion such as a chemically modified, for example crosslinked, film portion, a thickened film portion, a reinforced film portion in which for example a stiffening strip is adhered to the non-adhesive side of the film or by attaching a stiffer adhesive coated layer, for example an adhesive coated strip, to the end portion of the film.

Favoured dressings of the invention have a stiffened end portion which comprise an adhesive coated strip attached to the non-adhesive side of the film at this end portion. The adhesive coated strip may be coterminous with the film at the end portion in which case it is not necessarily stiffer than the film. Alternatively, an adhesive strip which is stiffer than the adhesive coated film can be adhered in an overlapping manner to the edge of the film to form the stiffened end portion of the dressing.

The major portion of the dressing is supported and in contact with the upper member. This portion can have a similar size to that of the upper member so that it is coterminous therewith or has a smaller size for example in the length direction thereof.

The lower member of the applicator is adapted to be grasped so that it can be pulled to allow removal of the upper member during application of a major portion of the dressing to the skin. Desirably, the lower member is longer than the upper member to facilitate grasping and to inhibit contact with the dressing during application.

Advantageously the lower member of the applicator can be provided with a lip to accommodate or receive an end portion of the overlapping tab of the extended protector. Such a lip will temporarily anchor the protector so that the portion of dressing adhered thereto will be substantially flat and be inhibited from flapping and moving prior to use so prevent creasing or puckering of the dressing adjacent to the tab before application.

Similarly the lower member can be advantageously provided with a lip which accommodates the end portion of the upper member remote from the hinged end of the applicator. Such a lip will anchor the upper member so that portion of the dressing adhered thereto will lie substantially flat prior to use and be inhibited from flapping or moving.

When as hereinafter mentioned the dressing comprises a thin elastic film, the applicator upper and lower members adjacent to the hinge portion thereof can be advantageously provided with chamfered or tapered sides to inhibit excess or uneven stretching and possible creasing of the adhesive film sides adjacent to the hinge portion when the upper member is removed.

The dressing of the invention can be provided with a pad or medicament area located on the adhesive side of the coated film.

The pad can be an absorbent pad suitable for absorbing exudate from wounds and dermatological disorders such as cold sores. Alternatively, or in addition, the pad can be a carrier for a medicament such as topical active medicament for the treatment of wounds or dermatological disorders. Such a medicament, however, can be provided on or within an adhesive area of the dressing.

In order to prevent contamination of the remaining adhesive surface of the dressing, it is preferred that the medicament is in the medicament area of the dressing, is present in a dry form such as particulate, film or sheet form.

Suitable topically active medicament for use in the invention includes topical antibacterials such as chlorhexidine salts, silver sulphadiazine, topical viricides such as Acyclovir (Trade mark) available from Wellcome Foundation and topical anaesthetics such as amethocaine.

The medicament, however, can be pharmacologically active agent which has a systemic effect when absorbed via the skin or mucosa. Suitable pharmacologically active agents include any of those suitable for transdermal or transmucosal delivery. Suitable pharmacologically active agents of this type are disclosed in European Patent Application No. 0250125. Particularly suitable agents for transdermal delivery are nitroglycerin, oxybutynin and phenazazocine.

The pharmacologically active agent will be carried on a pad which will release the agent when placed adjacent to skin. Suitable pads include the fiber mats and in particularly the polyurethane fiber mats disclosed in the hereinabove mentioned European Patent Application.

The pad or medicament area can conveniently be located in a central position of the adhesive surface of the dressing which is covered by the upper member. Favoured dressings of the invention comprise a rectangular pad which is located thereon with one edge adjacent to the folded hinge of the applicator members. Such a location of the pad on the adhesive surface of the dressing inhibits uneven stretching or creasing of the adhesive film sides adjacent to the folded hinge when upper member is removed.

Dressings of the invention preferably comprise a transparent or translucent adhesive coated film. Such dressings can advantageously have an applicator means which allow the pad or medicament area to be located over the skin treatment site.

In one favoured embodiment of the invention the upper and lower members of the applicator are sufficiently transparent or translucent to allow the pad or medicament area to be aligned with the treatment site prior to the application of the dressing.

In a second favoured embodiment of the invention the upper and lower members of the applicator each have an aperture which is aligned with the pad or medicament area to allow the pad or medicament area to be aligned with the treatment site prior to the application of the dressing.

Dressings of the invention which comprise a pharmacologically active agent will normally be impermeable to the agent and also to moisture vapour to promote absorption of the drug through the skin. Such impermeability properties can conveniently be provided by a suitable backing film. Suitable impermeable backing films for dressings of this type are disclosed in European Patent Application No. 0250125.

Dressings of the invention are preferably moisture vapour permeable to inhibit maceration of the skin in use.

Moisture vapour permeable dressings of the invention can suitably have a moisture vapour transmission rate of at least 300 g/m$^2$/24h, more suitably at least 500/m$^2$/24h and preferably at least 700 g/m$^2$/24h at 37° C. at 100% to 10% relative humidity difference. The moisture vapour transmission rate of an adhesive dressing can be readily determined by the Payne Cup Method (in the upright position) described in European Patent No. 46071.

The adhesive coated thin film of moisture vapour permeable dressing of the invention may contain apertures such as perforations to render the dressings permeable to liquids such as water.

Dressings of the invention, however, are preferably bacteria-proof in use to inhibit bacteria penetrating therethrough to the treatment site.

Films for use in the invention can be any of the thin flexible films used as backings for wound dressings.

Favoured flexible films are elastomeric moisture vapour permeable films. Suitable films of this page are disclosed in British Pat. No. 1280631 and European Pat. No. 91800.

Favoured elastomeric moisture vapour permeable films include those formed from polyether polyurethane, polyester polyurethane, hydrophilic polyurethane and polyester-polyether copolymers.

Suitable polyether polyurethanes are described in U.S. Pat. No. 2899411. Suitable polyester polyurethanes are described in U.S. Pat. No. 2871218. Apt polyester and polyether polyurethanes are known Estane (Trade mark) available from B. F. Goodrich and in particular grades 5701, 5702, 5703, 5714F and 580201.

An apt polyester-polyether copolymer is known as Hytrel 4056 available from Dupont.

Suitable hydrophilic polyurethane films for use in the inventions are disclosed in European Pat. No. 91800.

The thickness of the films used in the invention can suitably be 9 to 80=m, more suitable 15 to 50$\mu$m and can preferably be 20 to 40$\mu$m for example 30$\mu$m.

The moisture vapour permeable films used in the invention can suitably have a moisture vapour transmission rate of at least 300 g/m$^2$/24h, more suitably at 500 g/m$^2$/24h and can preferably have a moisture vapour transmission rate of at least 700 g/m$^2$/24h at 37° C. at 100 to 10% relative humidity difference.

The adhesive coating used in the dressing of the invention can be any of the pressure sensitive adhesives used on conventional wound dressings.

The adhesive coating can suitably have a thickness of 15 to 65$\mu$m, and can preferably have a thickness of 20 to 40$\mu$m. Such adhesive coatings will generally have a weight per unit area of 10 to 75 g/m$^2$, more usually of 15 to 65 g/m$^2$ and will preferably have a weight per unit area of 20 to 40 g/m$^2$.

The adhesive coating can be a continuous or a discontinuous coating for example a pattern, porous or microporous coating.

The adhesive coating however, is preferably continuous and moisture vapour permeable. Suitable adhesives for this type of coating are disclosed in British Pat. 1280631, United Kingdom Application No. 2040631 and European Patent Applications No. 35399. Favoured adhesives are polyvinyl ether adhesives and acrylic adhesives. An apt acrylic adhesive comprising a copolymer of 47 parts by weight of butyl acrylate, 47 parts by weight of butyl acrylate, 47 parts by weight of 2-ethylhexylacrylate and 6 parts by weight of acrylic is disclosed in United Kingdom Patent No. 2070631.

Moisture vapour permeable continuous adhesive coatings used in the invention can suitably have a moisture vapour transmitting rate of at least 300 g/m²/24h, desirably at least 500 g/m²/24h and preferably at least 700/m²/24h at 37° C. at 100 to 10% relative humidity difference.

The adhesive coated strip used to provide the stiffened end portion of the dressing of the invention can suitably be a strip material coated with a pressure sensitive adhesive suitable for adhesive dressings.

Suitable strip materials for use in the invention include those disclosed in the aforementioned United Kingdom Application No. 2157955 for the handles of the adhesive dressings described therein.

Favoured strip materials comprise an integral net. Preferred integral nets include those described in British Patent No. 1531715.

The adhesives used on the adhesive coated strips are favourably those described in relation to the adhesive dressing of the invention.

The protector used in the invention may be any of the flexible release materials used to protect the adhesive surface of a conventional adhesive dressing. Suitable protectors include plastics films such as polyethylene, polypropylene or unplasticised polyvinyl chloride, paper sheets and coated paper sheets which have been treated with a release agent such as silicone resin.

The upper member of the applicator can conveniently comprise a flexible release material similar to that used for the protector.

The lower member of the applicator can comprise a cardboard sheet or stiff plastics sheet portion.

The flexible film adhesive coated dressings of the invention include wound dressings for example those suitable for the treatment of cuts, ulcers, burns, abrasions or dermatological disorders, surgical drapes, catheter fixing dressings and transdermal drug devices. The dressings may be of large or medium size. The dressing and applicator of the invention, however, are highly suitable for small dressings such as first aid dressings, dressings for dermatological disorders such as spots or cold sores and dressings for fixing IV catheters in place. The dressing can conveniently be rectangular and have a length or width dimension of up to 12 cm for example 10 cm×5 cm, 9 cm×6 cm, 7 cm×5 cm and 2.5 cm×2 cm.

The dressings are preferably sterile within a bacteria proof pack.

Suitable methods for forming the adhesive coated films and adhesive coated strips used in the invention are disclosed in aforementioned United Kingdom Patent Application No. 2157955.

In one embodiment of the invention, the applicator can be formed either by attaching a stiff sheet to release sheet and folding the release sheet to provide a hinge or by attaching the release sheet and stiff sheet separately to an intermediate hinge member. Where the stiff sheet is attached directly to the release sheet it can be attached to a marginal portion or over a substantial proportion thereof to provide a reinforcement for the release sheet. The stiff sheet can be attached to either face of the release sheet by a conventional heat sealing or adhesive method. Where necessary a marginal portion of the card can be left non-adhered to the release sheet to provide a lip for accommodating an end portion of the protector or upper member of the applicator.

In an alternative embodiment of the invention, the applicator may be of unitary construction, folded over to provide the upper and lower members hinged at the fold, and made from suitable release sheet. The lower member may be reinforced or stiffened by lamination of or impregnation by another suitable material.

The adhesive dressing of the invention can then be formed by adhering a major proportion of the adhesive coated film to the upper member which forms a protector layer so that a marginal proportion projects beyond the hinge and covering the adhesive surface of the marginal proportion with a protector. An adhesive strip can be adhered to the non-adhesive side of the film at the marginal portion to form a stiffened end portion. Alternatively the adhesive coated film can be applied to the upper member without projecting beyond the hinge and the adhesive strip is adhered to the edge of the dressing to form a projecting stiffened end portion.

The applicator can be provided with chamfered edges by cutting by a conventional method the sides of applicator adjacent to hinge at angle which reduces the length of the hinge.

The lower and upper members of the applicator can be provided with aligned apertures by a conventional die cutting method.

The invention will now be illustrated with reference to the following drawings in which FIG. 1 is a cross section of a preferred dressing of the invention.

Figure 1:
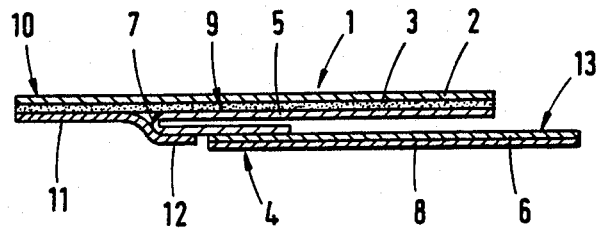

FIG. 1 shows a dressing of the invention (1) having a thin film (2) coated with adhesive (3) and an applicator (4) therefor. Applicator (4) comprises a pair of superposed laminar members (5, 6) having folded hinge (7) at one end. The lower member (6) is laminated to portion (8) to render it more stiff than the upper member (5). Upper member (5) releasably supports the dressing (1) and provides a flexible protector layer for a major portion (9) of the surface of adhesive (3) of dressing (1).

End portion (10) of dressing (1), which extends beyond folded hinge end (7) has its adhesive surface covered by a protector (11) which has a tab (12) to facilitate removal thereof Tab (12) is shown in FIG. 1 overlapping the applicator (4) at the folded hinge end (7).

As shown in the embodiment illustrated in FIG. 1, lower member (6) is longer than upper member (5) and its end (13) remote from hinge (7) extends beyond the end of the dressing to facilitate grasping during application of the dressing. The dressing of FIG. 1 can be applied to the skin by removing protector (11) from end portion (10) of the adhesive by means of tab (12), adhering end portion (10) to the skin to anchor the dressing at one end and then gradually peeling back upper member (5) from portion (9) of the adhesive surface by pulling stiff portion (8) of lower member (6) in the direction of end (13) thereof and thereafter adhering portion (9) to the skin.

Portion (8) of lower member (6), because of its stiff nature can act as a handle to facilitate accurate positioning and initial anchoring of end portion of the adhesive dressing without undue handling thereof and inhibits the upper member from twisting during its removal from the remainder of the adhesive surface so that the dressing can be applied to the skin without substantial creasing or puckering. Furthermore such an application of the dressing advantageously can be achieved by grasping the lower member in one hand.

Figure 2:
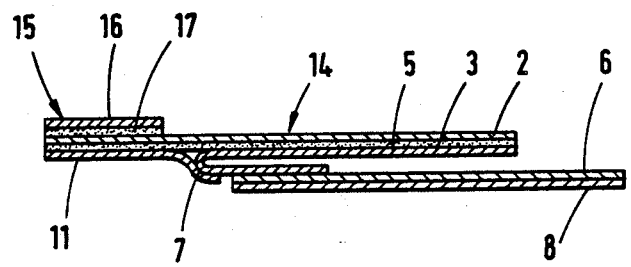
FIG. 2 is a cross section of a dressing similar to FIG. 1 with a stiffened end portion.

FIG. 2 shows a dressing (14) similar to that of FIG. 1 in which the end portion (15) is stiffened with a strip (16) coated with a adhesive (17) and adhered to the non-adhesive side of film 2.

Figure 3:
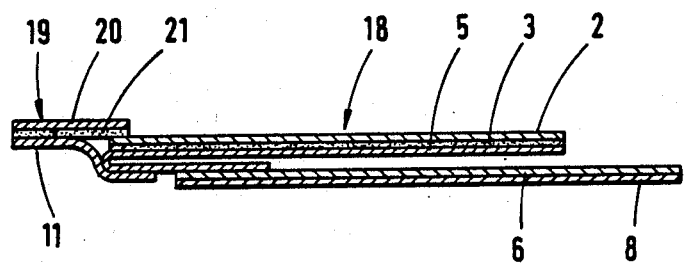
FIG. 3 is a cross section of a dressing similar to FIG. 1 with alternative stiffened end portion.

FIG. 3 shows a dressing (18) similar to that of FIG. 1 with a stiffened end portion (19) in the form of a strip (20) coated with adhesive (21) which overlaps and is adhered to the non-adhesive surface of film 2.

The stiffened portions (15, 19) of dressings (14, 18) of FIGS. 2 and 3 do not "flop" or "droop" when second protector layer (11) is removed. Such stiffened portions, therefore, will facilitate initial application of the dressing to the skin.

Figure 4:
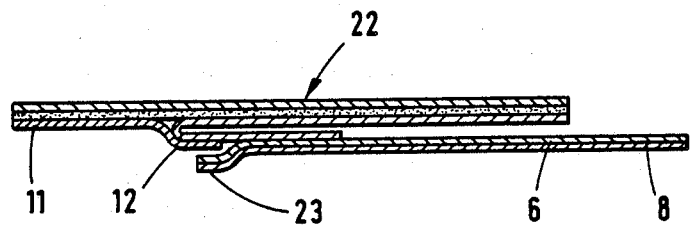
FIG. 4 is a cross section of a dressing similar to FIG. 1 in which the lower member is provided with a lip to accommodate the protector.

FIG. 4 shows a dressing (22) similar to that of FIG. 1 in which lower member (6) is provided with a lip (23) to accommodate an end portion of tab (12) of protector (11).

Figure 5:
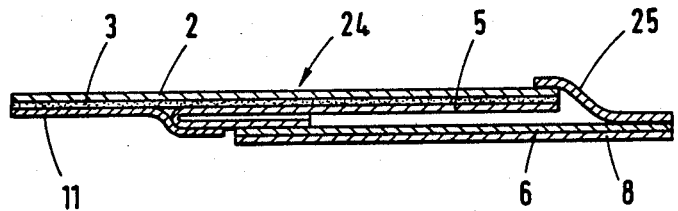
FIG. 5 is a cross section of a dressing similar to FIG. 1 in which the lower member has a lip to accommodate the upper member.

FIG. 5 shows a dressing (24) similar to that of FIG. 1 in which lower member (6) has a lip (25) which can accommodate an end portion of upper member (5).

FIGS. 4 and 5 shows the end portion of tab (12) and the end portion of upper member (5) within respective lips (23, 25). In such an arrangement because of the stiff nature of lower member (6) tab (12) and/or upper member (5) are temporarily maintained in a flat position and inhibited from "flapping" or moving prior to use.

Figure 6:
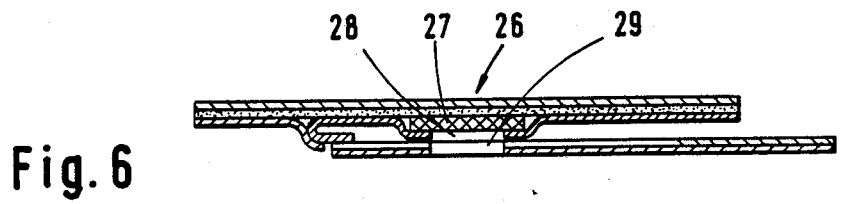
FIG. 6 is a cross section of a dressing similar to FIG. 1 with a pad containing medicament.
Figure 7:
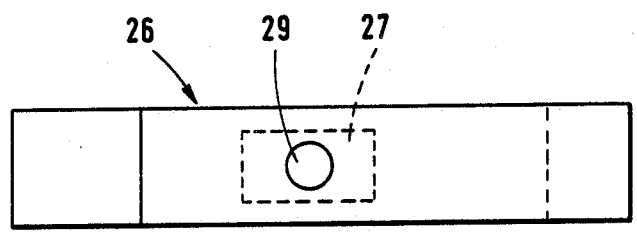
FIG. 7 is a plan view of the dressing of FIG. 6 from the underside thereof.

FIGS. 6 and 7 show a dressing (26) similar to that of FIG. 1 in which dressing (26) has a rectangular pad (27) containing medicament centrally located the surface of its adhesive (3) and circular apertures (28, 29) in upper and lower members (5, 6) respectively. Apertures (28, 29) as shown in FIG. 6 are aligned with pad (27) so that the pad can be positioned over the skin are to be treated prior to application of dressing (26).

Figure 8:
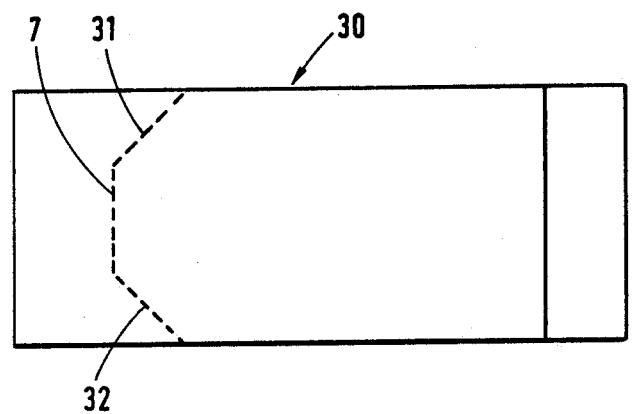
FIG. 8 is a top view of a dressing similar to that of FIG. 1 in which the applicator has chamfered sides.

FIG. 8 shows a dressing (30) similar to that of FIG. 1 in which the sides of applicator members (5, 6) adjacent to the folded hinge (7) has chamfered edges (31, 32). Such chamfered sides can inhibit undue stretching of the side edges of film (2) when upper member (5) is removed and thus can also inhibit creasing caused by such stretching or retraction of the film.

Figure 9:
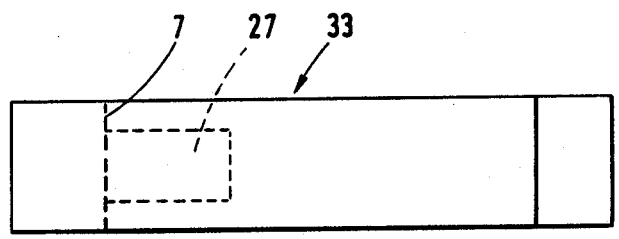
FIG. 9 is a top view of dressing similar to that of FIG. 6.

FIG. 9 shows a dressing (33) similar to that of FIG. 7 in which rectangular pad (27) is located with one edge adjacent to folded hinge (7) of the applicator members. Such an arrangement of the pad allows dressing 33 to be removed from upper member 5 without creasing or puckering of thin film (2) adjacent to the sides of the pad.

The invention will now be illustrated by reference to the following examples.

EXAMPLE 1

Preparation of a Dressing of the Invention Suitable for Wounds or IV Catheters

An applicator for the dressing was formed by heat sealing one end of a rectangular (9.5 cm×5.0 cm) release sheet of plastic coated layer to an end marginal portion of a rectangular (5.5 cm×5 cm) cardboard sheet and folding the attached sheets to form an upper release member (length 6 cm) and lower member (length 7.7 cm) with a stiff portion (5.5 cm).

A rectangular adhesive dressing (7 cm×5 cm) was adhered onto the upper release member so that an end marginal portion (1 cm) of dressing extended beyond the hinge. The adhesive surface of this portion was then covered with release strip (width 3.3 cm) which overlapped the hinge to provide a tab.

The adhesive dressing used in this example comprised a thin film (30μm) of polyurethane (Estane 5714) coated with a polyvinyl ether adhesive (30 g./m²). The adhesive dressing was formed and adhered onto the release sheet of the applicator by the general methods given in Example 1 of United Kingdom Patent Application No. 2157955.

EXAMPLE 2

An adhesive dressing and applicator was formed in the same manner as Example 1 except that a marginal end portion of the adhered cardboard sheet Was not adhered to the release sheet to provide a lip adjacent to the hinge to accommodate an end portion of the release strip. It was found that when the end portion of the release strip was coated within the lip the release strip was maintained aligned with stiff member and was prevented from "flapping" prior to use.

EXAMPLE 3

An adhesive dressing and applicator was formed in the same manner as Example 1 except that the side edges of the applicator adjacent to the folded hinge were chamfered by cutting into the hinge to inhibit creasing when the upper release sheet was removed.

EXAMPLE 4

A rectangular adhesive dressing and applicator were formed in the same manner as Example 1 except that the applicator had a rectangular lower stiff member (length 8 cm) connected via the hinge to an upper release member (length 7 cm) which completely covered the adhesive surface of the film portion of the dressing and the adhesive dressing had a reinforced end portion provided by an adhesive strip (2.5 cm) which is adhered to a marginal portion thereof in a overlapping manner to provide a portion (1 cm) which extends beyond the hinge.

The adhesive strip used in this example had a fibrillated backing coated with an acrylate adhesive (30 g./m²) and was formed by the method given in British Pat. No. 153715. The acrylate adhesive comprised a copolymer of 47 parts by weight butyl acrylate 47 parts by weight 2 ethylhexyl acrylate and 6 parts by weight acrylic acid prepared by the method given in United Kingdom Pat. No. 2070631.

EXAMPLE 5

An adhesive dressing was formed in the same manner as Example 1 with the following modifications.

The adhesive dressing had a size of 2.5 cm×2 cm and had a medicament in particulate form applied as a circular area (diameter 0.5 cm) on a central portion of the adhesive surface of the dressing. The upper release member (2 cm×2 cm) covered a major proportion of the dressing to leave an end margin (0.5 cm) to be covered by the release strip (2.5 cm×2.5 cm). The upper release member was attached via the hinge to a lower member (7.5 cm) having a stiff cardboard portion (5.5 cm). The lower member had a lip on its upper side, provided by the end portion stiff member adjacent to the hinge being left unadhered, to accommodate an end portion of the upper member.

Both the upper and lower members had circular apertures (0.5 cm) which were aligned with the medicament area on the dressing.

The dressing of this example, when provided with a suitable medicament, is suitable for the treatment of dermatological disorders such as spots and cold sores. It was found that the apertures in the upper and lower members of applications allowed the dressing to be applied accurately over the area to be treated.

EXAMPLE 6

An adhesive dressing and applicator was formed in the same manner as Example 1 with the following modifications.

The rectangular adhesive dressing (3.5 cm×2 cm) had a rectangular absorbent pad (1 cm×1 cm) of spray hydrophilic polyurethane fiber mats (weight per unit area 175 g./m²) on its adhesive surface.

The polyurethane fiber mat of the pad was made according to the method given in Example 1 of European Patent Application No. 0250125. The upper release member (3.5 cm×2 cm) covered a major proportion of the dressing to leave an end margin (0.5×2 cm) covered by the release protector (2.5 cm×2 cm). The upper release member was attached via a folded hinge to a lower member (9 cm×2 cm) having a flexible portion (4 cm×2 cm) and attached to stiffer cardboard portion (5 cm×2 cm) in overlapping manner. The lower member had a lip on its upper side, provided a non-adhered end part of the stiffer cardboard portion adjacent to the hinge, to accommodate an end portion of the upper member.

The pad of the dressing was located with one side thereof adjacent to the folded hinge.

The dressing of this example had a absorbent pad suitable for carrying a pharmacologically active agent which has a systemic effect when absorbed via the skin or mucosa such as those disclosed in European Patent Application No. 0250125.

All the dressings of Examples 1 to 6 could be simply applied to the skin by removing the strip release sheet to expose the marginal end portion of adhesive, adhering the end portion to the skin to provide and anchor and then pulling the stiff portion of the lower member to remove the upper release member and adhere the dressing to the skin. It was found that these dressings after being anchored could be applied by one hand without any substantial creasing or puckering.

I claim:

1. An adhesive coated thin film dressing in combination with an applicator therefor wherein the applicator comprises a pair of superposed laminar members hinged at one end, the lower member being adapted to be grasped at the end remote from the hinge and the upper member being adapted to support the dressing and being in releasable contact with a major portion of the adhesive surface thereof; and wherein a protector, in releasable contact with the remaining portion of the adhesive surface, extends beyond the hinged end of the upper member.

2. A combination according to claim 1 in which the lower member of the applicator is of a rigidity to support the upper member bearing the dressing.

3. A combination according to claim 1 in which the lower member is longer than the upper member.

4. A combination according to claim 1 in which the protector covers a marginal end portion of adhesive surface of the dressing.

5. A combination according to claim 1 in which the protector extends beyond the adhesive surface.

6. A combination according to claim 5 in which the extended protector overlaps the lower member.

7. A combination according to claim 6 in which the lower member has a lip to receive the extended protector.

8. A combination according to claim 3 in which the lower member has a lip to accommodate the end portion of the upper member remote from the hinge end.

9. A combination according to claim 1 in which the dressing has a medicament pad or a medicament area located on the adhesive side of the coated film.

10. A combination according to claim 9 in which the medicament is a antibacterial or viricide.

11. A combination according to claim 9 in which the medicament is a pharmacologically active agent which has a systemic effect when absorbed via skin or mucosa.

12. A combination according to claim 9 which is sufficiently transparent or translucent to allow the medicament pad or area to be aligned with the treatment site prior to application of the dressing.

* * * * *